(12) United States Patent
Anissian (10) Patent No.: US 10,478,306 B1
(45) Date of Patent: Nov. 19, 2019

(54) MATERIALS AND METHODS FOR PREVENTION OF COLD WELDING, CORROSION AND TISSUE OVERGROWTH BETWEEN MEDICAL IMPLANT COMPONENTS

(71) Applicant: Lucas Anissian, Lake Oswego, OR (US)

(72) Inventor: Lucas Anissian, Lake Oswego, OR (US)

( * ) Notice: Subject to any disclaimer, the term of this patent is extended or adjusted under 35 U.S.C. 154(b) by 0 days.

(21) Appl. No.: 15/727,699

(22) Filed: Oct. 9, 2017

Related U.S. Application Data

(62) Division of application No. 14/330,634, filed on Jul. 14, 2014, now Pat. No. 9,782,260.

(51) Int. Cl.
*A61B 17/80* (2006.01)
*A61F 2/34* (2006.01)
(Continued)

(52) U.S. Cl.
CPC ............. *A61F 2/34* (2013.01); *A61B 17/809* (2013.01); *A61F 2/30767* (2013.01); *A61B 2017/00836* (2013.01); *A61F 2002/3006* (2013.01); *A61F 2002/30051* (2013.01); *A61F 2002/30932* (2013.01); *A61F 2002/3432* (2013.01); *A61F 2210/0009* (2013.01); *A61F 2220/0016* (2013.01); *A61F 2240/00* (2013.01); *A61F 2250/0054* (2013.01)

(58) Field of Classification Search
CPC ...... A61F 2002/3432; A61F 2250/0054; A61F 2002/30107; A61F 2002/30051; A61F 2210/0009; A61F 2/30771; A61B 2017/00836; A61B 17/80
See application file for complete search history.

(56) References Cited

U.S. PATENT DOCUMENTS

3,987,499 A 10/1976 Scharbach et al.
4,227,265 A 10/1980 Frey
(Continued)

*Primary Examiner* — David H Willse
*Assistant Examiner* — Javier G Blanco
(74) *Attorney, Agent, or Firm* — R. Keith Harrison (57) ABSTRACT

Methods for prevention of cold welding and/or corrosion between and/or tissue/bone overgrowth on implant components may include obtaining a first medical implant component having a first implant contact surface; obtaining a second medical implant component having a second implant contact surface, the second implant contact surface adapted for placement into contact with the first implant contact surface, the first implant contact surface and the second implant contact surface encompassing all points of contact between the first medical implant component and the second medical implant component; and applying a nonmetallic biocompatible separation coating material having a wax formulation on at least one of the first implant contact surface and the second implant contact surface, the nonmetallic biocompatible separation coating material separates the first implant contact surface from the second implant contact surface at all of the points of contact between the first medical implant component and the second medical implant component. Medical implant for prevention of cold welding, corrosion and tissue overgrowth on medical implant components are also disclosed.

4 Claims, 4 Drawing Sheets

(51) Int. Cl.
*A61F 2/30* (2006.01)
*A61B 17/00* (2006.01)

(56) References Cited

U.S. PATENT DOCUMENTS

| | | | |
|---|---|---|---|
| 5,282,746 | A | 2/1994 | Sellers et al. |
| 6,296,667 | B1 | 10/2001 | Johnson et al. |
| 2002/0111590 | A1 | 8/2002 | Davila et al. |
| 2006/0257354 | A1* | 11/2006 | Fechtenkotter ....... C08F 210/02 424/78.27 |
| 2009/0198286 | A1 | 8/2009 | Lozier et al. |
| 2010/0286776 | A1 | 11/2010 | Anderson |

* cited by examiner

MATERIALS AND METHODS FOR PREVENTION OF COLD WELDING, CORROSION AND TISSUE OVERGROWTH BETWEEN MEDICAL IMPLANT COMPONENTS

CROSS-REFERENCE TO RELATED APPLICATIONS

This is a divisional of parent U.S. application Ser. No. 14/330,634, now U.S. Pat. No. 9,782,260, filed Jul. 14, 2014 and entitled MATERIALS AND METHODS FOR PREVENTION OF COLD WELDING, CORROSION AND TISSUE OVERGROWTH BETWEEN MEDICAL IMPLANT COMPONENTS, which claims the benefit of U.S. provisional application No. 61/933,068, filed Jan. 29, 2014 and entitled MATERIALS AND METHODS FOR PREVENTION OF COLD WELDING, CORROSION AND TISSUE OVERGROWTH BETWEEN MEDICAL IMPLANT COMPONENTS, each of which provisional application and parent application is incorporated by reference herein in its entirety.

FIELD

Illustrative embodiments of the disclosure are generally directed to prosthetic implants used to replace and/or augment a bodily function or lack of function. More particularly, illustrative embodiments of the disclosure relate to materials and methods for prevention of cold welding, corrosion in interfaces between implant components and tissue overgrowth on surfaces of implants.

BACKGROUND

The background description provided herein is solely for the purpose of generally presenting the context of the illustrative embodiments of the disclosure. Aspects of the background description are neither expressly nor impliedly admitted as prior art against the claimed subject matter.

Medical implants such as joint prostheses and the like are frequently used to replace and/or restore a bodily function or lack of function. For example, hip prosthesis systems may replace the hip joint in patients who have lost some or all of the function of the original joint. The implant components may be metal or alloy and are typically secured to bone using metal or alloy fasteners. Thus, there may be a risk of fusion caused by cold welding and/or corrosion between metallic or alloyed surfaces on adjacent medical implant components. Another unwanted event which makes the removal of implants difficult is tissue overgrowth on the implants. In some procedures such as bone fracture repairs, the implants may be subsequently removed or extracted from the bone after healing. Cold welding or corrosive fusion between the medical implant components or between a component and a fastener, or tissue/bone overgrowth on the implants, may render the extraction process difficult.

Accordingly, materials and methods for prevention of cold welding, corrosion in interfaces between implant components and tissue overgrowth on surfaces of implants may be useful for some applications.

SUMMARY

Illustrative embodiments of the disclosure are generally directed to methods for prevention of cold welding and/or corrosion between and/or tissue/bone overgrowth on implant components. An illustrative embodiment of the methods includes obtaining a first medical implant component having a first implant contact surface; obtaining a second medical implant component having a second implant contact surface, the second implant contact surface adapted for placement into contact with the first implant contact surface, the first implant contact surface and the second implant contact surface encompassing all points of contact between the first medical implant component and the second medical implant component; and applying a nonmetallic biocompatible separation coating material having a wax formulation on at least one of the first implant contact surface and the second implant contact surface, the nonmetallic biocompatible separation coating material separates the first implant contact surface from the second implant contact surface at all of the points of contact between the first medical implant component and the second medical implant component.

Illustrative embodiments of the disclosure are further generally directed to methods of sealing an interface between a first implant component and a second implant component in a prosthesis system. An illustrative embodiment of the methods includes placing a first medical implant component having a first implant contact surface and a second medical implant component having a second implant contact surface into contact with each other, the first implant contact surface and the second implant contact surface encompassing all points of contact between the first medical implant component and the second medical implant component; and imparting a fluid-tight seal at an interface between the first implant contact surface of the first medical implant component and the second implant contact surface of the second medical implant component by applying a nonmetallic biocompatible separation coating material having a wax formulation between the first implant contact surface and the second implant contact surface, the nonmetallic biocompatible separation coating material separates the first implant contact surface from the second implant contact surface at all of the points of contact between the first medical implant component and the second medical implant component.

Illustrative embodiments of the disclosure are further generally directed to medical implants for prevention of cold welding, corrosion and tissue overgrowth on medical implant components. An illustrative embodiment of the medical implants includes an implant plate having a first implant contact surface. At least one fastener having a second implant contact surface may positionally interface with the first implant contact surface of the implant plate. The first implant contact surface and the second implant contact surface may encompass all points of contact between the implant plate and the at least one fastener. A nonmetallic biocompatible separation coating material may be provided on at least one of the first implant contact surface and the second implant contact surface. The separation coating material may include a wax and imparts a coating layer at an interface between the first implant contact surface of the implant plate and the second implant contact surface of the at least one fastener. The separation coating material may separate the implant plate from the at least one fastener at all points of contact between the implant plate and the at least one fastener. The separation coating material may be formulated to prevent cold welding, corrosion, and tissue overgrowth between the first medical implant component and the second medical implant component.

BRIEF DESCRIPTION OF THE DRAWINGS

Illustrative embodiments of the disclosure will now be described, by way of example, with reference to the accompanying drawings, in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable users skilled in the art to practice the disclosure and are not intended to limit the scope of the claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description. Relative terms such as "front" and "rear" are used in aid in an understanding of the illustrative embodiments of the methods and are not intended to be construed in a limiting sense.

Illustrative embodiments of the disclosure are generally directed to materials and methods for prevention of cold welding, corrosion and tissue overgrowth between medical implant components. In some embodiments, the materials for prevention of cold welding, corrosion and tissue overgrowth between medical implant components medical implants. The implants for prevention of cold welding, corrosion and tissue overgrowth between implant components may include a first medical implant component having a first implant contact surface; a second medical implant component having a second implant contact surface positionally interfacing with the first implant contact surface of the first medical implant; and a biocompatible separation coating material on at least one of the first implant contact surface and the second implant contact surface.

In some embodiments, the first medical implant component may include an acetabular shell and the second medical implant component may include a fastener.

In some embodiments, at least one fastener opening may be provided in the acetabular shell. The first implant contact surface may be in the fastener opening or fastener openings.

In some embodiments, the second implant contact surface of the second medical implant may include metal or alloy fastener contact surfaces on the fastener.

In some embodiments, the first medical implant component may include an implant plate and the second medical implant component may include a fastener.

In some embodiments, a plurality of fastener openings may be provided in the implant plate, and the first implant contact surface may be in each of the plurality of fastener openings.

In some embodiments, second implant contact surface of the second medical implant may include metal or alloy fastener contact surfaces on the fastener.

In some embodiments, the separation coating material may be provided on the first implant contact surface and the second implant contact surface.

In some embodiments, the biocompatible separation coating material may include an ethylene and copolymer wax.

Illustrative embodiments of the disclosure are further generally directed to methods for prevention of cold welding and/or corrosion between and/or tissue/bone overgrowth on implant components. An illustrative embodiment of the methods includes obtaining a first medical implant component having a first implant contact surface; obtaining a second medical implant component having a second implant contact surface, the second implant contact surface adapted for placement into contact with the first implant contact surface; and applying a separation coating material on at least one of the first implant contact surface and the second implant contact surface.

Figures 1, 1A, 2, 2A:
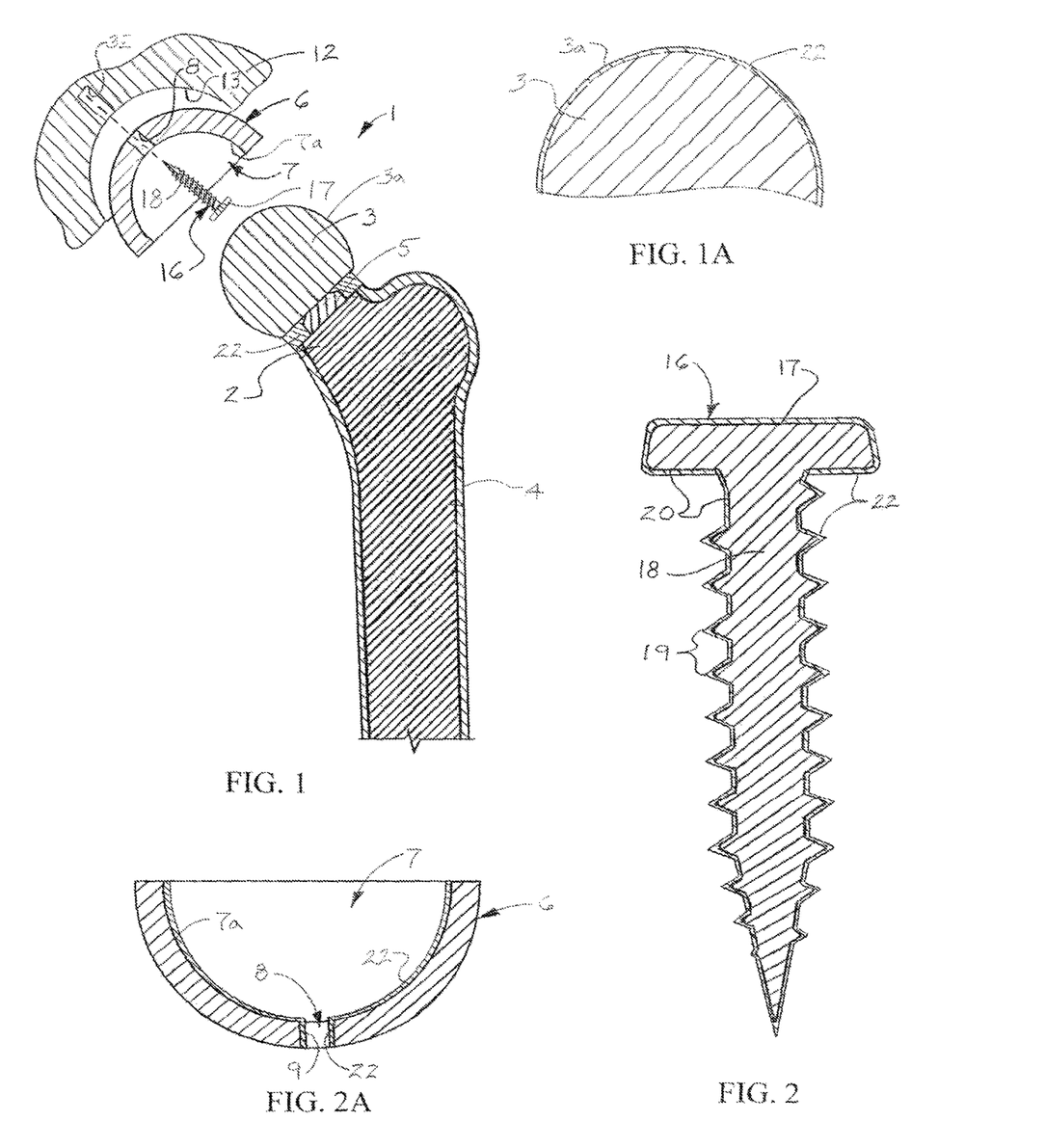
FIG. 1 is an exploded sectional view of an exemplary hip prosthesis system in implementation of an illustrative embodiment of the methods for prevention of cold welding, corrosion and/or tissue overgrowth on or between medical implant components.
FIG. 1A is an enlarged sectional view of a typical prosthetic head component of the exemplary hip prosthesis system.
FIG. 2 is a longitudinal sectional view of an exemplary implant fastener of the hip prosthesis system, treated according to an illustrative embodiment of the methods for prevention of cold welding, corrosion and/or tissue overgrowth on or between medical implant components.
FIG. 2A is a sectional view of an exemplary acetabular shell of the hip prosthesis system, treated according to an illustrative embodiment of the methods for prevention of cold welding, corrosion and/or tissue overgrowth on or between medical implant components.

Referring initially to FIGS. 1-2A of the drawings, an exemplary hip prosthesis system 1 in implementation of an illustrative embodiment of the methods for prevention of cold welding, corrosion and tissue overgrowth between medical implant components, hereinafter methods, is illustrated in FIG. 1. The hip prosthesis system 1 is a non-limiting example of a medical implant which may be suitable for implementation of the methods. The hip prosthesis system 1 may include a femoral component 2 which is surgically implanted into a femur 4 of a patient. A typically metallic alloyed prosthetic head 3 fits on the femoral component 2. The prosthetic head 3 may be attached to the femoral component 2 via a bolt, screw or other attachment device 5. A typically metallic or alloyed acetabular shell 6 may be fastened into an acetabular cavity 13 in an acetabulum 12 of the patient. The acetabular shell 6 has an acetabular shell cavity 7 which receives a liner (not illustrated) to articulate with the prosthetic head 3 on the femoral component 2. Multiple fastener openings 8 may extend through the acetabular shell 6 to facilitate attachment of the acetabular shell 6 to the acetabular cavity 13 using multiple implant fasteners 16 which are typically metallic or alloyed. The acetabular shell 6 and the implant fasteners 16 may be the same or different metals or alloys.

As illustrated in FIG. 2, each implant fastener 16 may include a fastener head 17 and an elongated fastener shaft 18 which extends from the fastener head 17. Spiraled fastener threads 19 may extend from the fastener shaft 18. The fastener head 17, the fastener shaft 18 and the fastener threads 19 may have metal or alloy fastener contact surfaces 20. As illustrated in FIG. 2A, the acetabular shell 6 of the hip prosthesis system 1 may include a threaded metal or alloy implant contact surface 9 within each fastener opening 8.

According to some embodiments of the methods, a biocompatible separation coating material 22 may be coated on the fastener contact surfaces 20 on each implant fastener 16, as illustrated in FIG. 2. Additionally or alternatively, a biocompatible separation coating material 22 may be applied to the implant contact surface 9 (FIG. 2A) of each fastener opening 8 in the acetabular shell 6. As illustrated in FIG. 2A, the separation coating material 22 may additionally be applied to the interior cavity surface 7a of the acetabular shell 6 and/or to the exterior prosthetic head surface 3a of the prosthetic head 3, as illustrated in FIG. 1A. In some applications, the separating coating material 22 may be applied between the femoral component 2 and the prosthetic head 3. Thus, the separation coating material 22 seals the attachment device 5 and prevents fluid penetration and corrosion at the interface between the femoral component 2 and the prosthetic head 3. In assembly of the hip prosthesis system 1, the acetabular shell 6 is fastened in the acetabulum cavity 13 in the acetabulum 12 by extending the fastener shaft 18 of each implant fastener 16 through the corresponding fastener opening 8 and threading the fastener shaft 18 into a registering pre-drilled fastener cavity 32 in the acetabulum 12. A liner (not illustrated) may be inserted into the acetabular shell 6. By relocating the hip joint, the prosthetic head 3 will be placed in the acetabulum cavity 7 to complete assembly of the hip prosthesis system 1. It will be appreciated by those skilled in the art that the separation coating material 22 on the fastener contact surfaces 20 of each implant fastener 16 and/or on the implant contact surface 9 in each fastener opening 8 of the acetabular shell 6 maintains contact separation between the respective surfaces of the implant fasteners 16 and the acetabular shell 6, preventing cold welding, corrosion and/or tissue overgrowth on or between the respective surfaces throughout the lifetime of the hip prosthesis system 1. Therefore, in the event that the hip prosthesis system 1 subsequently requires replacement due to infection, for example, the implant fasteners 16 can be easily removed from the fastener openings 8 in the acetabular shell 6 and the fastener cavities 32 in the underlying acetabulum 12.

The separation coating material 22 may be compounded using any organic or inorganic and substantially nonmetallic biocompatible material which can be applied to the fastener contact surfaces 22 on the implant fasteners 16 and/or the implant contact surface 9 in the fastener openings 8 of the acetabular shell 6 to maintain separation between those respective surfaces. Non-limiting examples of materials which are suitable for the separation coating material 22 include any molecular weight ethylene and copolymer waxes containing from about 5 percent to about 99 percent by weight of a co-monomer with molecular weight in the range of from about 500 to about 5,000.000 Dalton, and any combination thereof. Other non-limiting examples of suitable materials for the separation coating material 22 include liquid, semisolid or solid hydrocarbons, monoesters, diesters, triesters, hydroxy monoesters, hydroxy polyesters, acid esters, acid polyesters, free acids, free alcohols, paraffin, petroleum jelly, esters, fatty acids, alcohol chains, palmitate, isopropyl palmitate or any combination thereof. Non-limiting examples of components and their concentrations which may be added to change some of the physical characteristics of the separation coating material 22 depending on the application include glycerol, glycolide, water, hyaluronic acid, D or L-lactide collagen or non-collagenous protein, lactic acid and/or glycolic acid dextran, chondroitin, chondroitin-4-sulfate, chondroitin-6-sulfate, heparin, heparan sulfate, keratan sulfate aqueous solution and any combination thereof. One non-limiting example of compounds which are suitable for the biocompatible separation coating material 22 includes any commercially-available sterile bone wax formulation which is commonly used to control bleeding from bone surfaces in surgical procedures.

In some embodiments, fabrication of the separation coating material 22 may include laboratory refinement of beeswax, in which case the separation coating material 22 may last for many years. However, changes may be made to the composition of the separation coating material 22 according to the knowledge of those skilled in the art to alter its longevity or absorption.

The separation coating material 22 may have a broad range of consistency and can be applied to the surfaces using smearing, spraying, immersion and/or other suitable technique. The separation coating material 22 may be applied to the surfaces at any stage of production including but not limited to during fabrication of the acetabular shell 6, the implant fastener 16 and/or other component or components of the implant or to the components before or during surgery. The separation coating material 22 prevents contact between the adjacent surfaces on the implant fasteners 16 and the acetabular shell 6 and/or between any other adjacent surfaces in the hip prosthesis implant 1 where static contact interaction between adjacent surfaces may lead to cold welding, and/or corrosion. The coating material disclosed can be applied to the surfaces on the implant according to the knowledge of those skilled in the art to prevent tissue or bone overgrowth.

Figures 3, 4, 5:
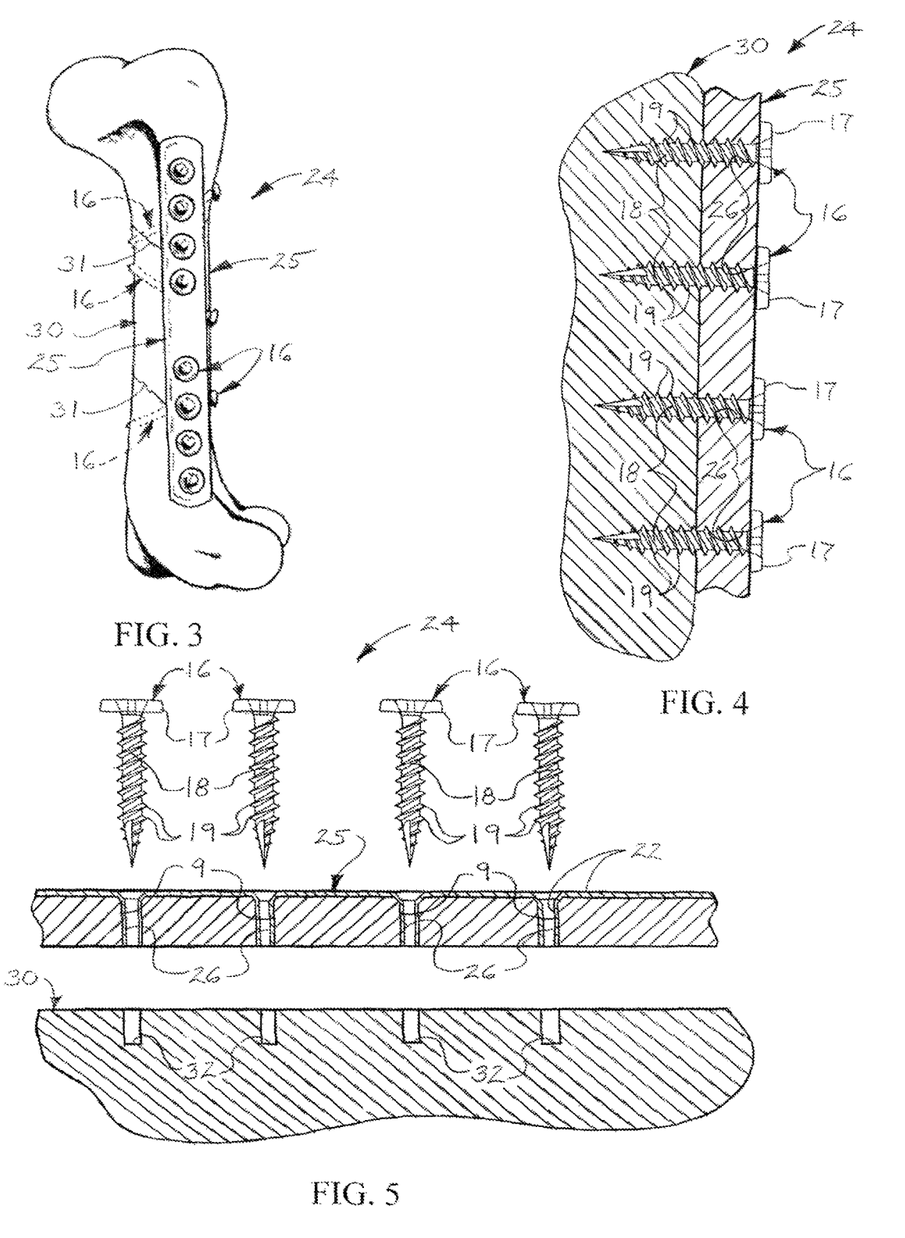
FIG. 3 is a side view of an exemplary bone fracture repair system in implementation of an illustrative embodiment of the methods for prevention of cold welding, corrosion and/or tissue overgrowth on or between medical implant components.
FIG. 4 is a side view of the exemplary bone fracture repair system fastened to bone.
FIG. 5 is an exploded side view of the exemplary bone fracture repair system treated according to an illustrative embodiment of the methods for prevention of cold welding, corrosion and/or tissue overgrowth on or between medical implant components.

Referring next to FIGS. 3-5 of the drawings, an exemplary bone fracture repair system 24 in implementation of an illustrative embodiment of the methods is illustrated. The bone fracture repair system 24 is a non-limiting example of a medical implant which may be suitable for implementation of the methods. As illustrated in FIG. 3, the bone fracture repair system 24 may be used to stabilize a bone 30 as one or more fractures 31 in the bone 30 heal. The bone fracture repair system 24 may include at least one elongated implant plate 25 which may include steel and/or other metal or alloy. Multiple fastener openings 26 (FIG. 4) which receive the respective implant fasteners 16 may extend through the implant plate 25 in spaced-apart relationship to each other. Multiple implant fasteners 16 may be inserted through the fastener openings 26 in the implant plate 25 and threaded into registering fastener cavities 32 in the underlying bone 30, typically in the conventional manner, to fasten the implant plate 25 to the bone 30 and stabilize the bone 30 as the fractures 31 heal. The implant plate 25 and the implant fasteners 16 may be the same or different metals or alloys. As illustrated in FIG. 5, prior to installation of the bone fracture repair system 24, a separation coating material 22 may be applied to the implant contact surface 9 of each fastener opening 26. Because bone tissue overgrowth may have a tendency to occur on the exterior surface of the implant plate 25, the separation coating material 22 may also be applied to at least a portion of the exterior surface of the implant plate 25. Additionally or alternatively, the separation coating material 22 may be provided on the fastener contact surfaces 20 (FIG. 2) of each implant fastener 16 as was heretofore described with respect to FIG. 2.

After installation of the bone fracture repair system 24, the implant plate or plates 25 stabilize the bone 30 as the fracture or fractures 31 heal typically over a period of several months. During this period, the separation coating material 22 maintains contact separation between the respective surfaces of the implant fasteners 16 and the implant plate 25, preventing cold welding, corrosion and/or tissue overgrowth on or between the respective surfaces as the bone fracture repair system 24 remains in place on the bone 30. Consequently, upon removal of the implant plate 25 from the bone 30, the implant fasteners 16 can be easily removed from the fastener openings 26 in the implant plate 25 and the fastener cavities 32 in the underlying bone 30.

Figure 6:
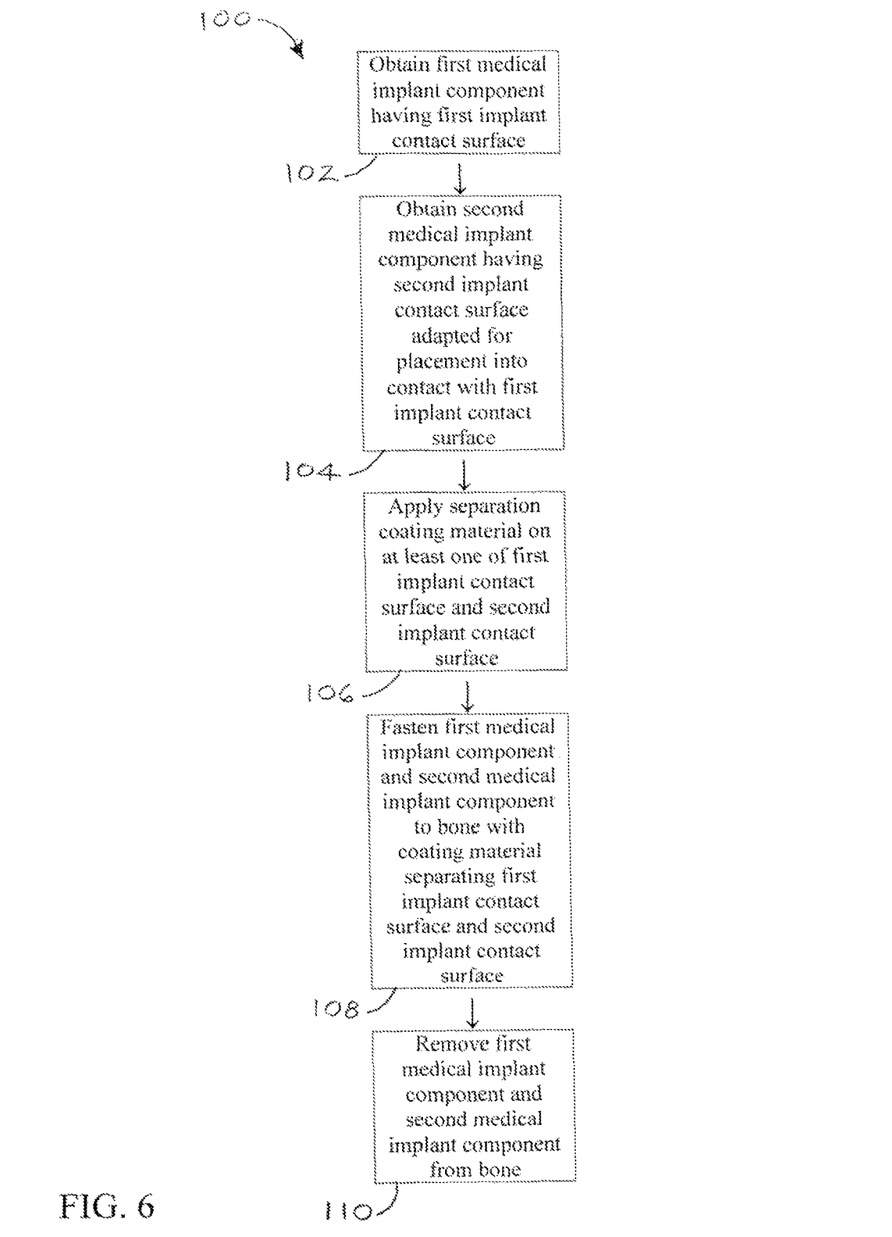
FIG. 6 is a flow diagram of an illustrative embodiment of the methods for prevention of cold welding, corrosion and/or tissue overgrowth on or between medical implant components.

Referring next to FIG. 6 of the drawings, a flow diagram 100 of an illustrative embodiment of the methods for prevention of cold welding, corrosion and tissue overgrowth between medical implant components is illustrated. At block 102, a first medical implant component having a first implant contact surface is obtained. At block 104, a second medical implant component having a second implant contact surface adapted for placement into contact with the first implant contact surface of the first medical implant component is obtained. In some embodiments, the first medical implant component may include an acetabular shell and the second medical implant component may include at least one implant fastener. In some embodiments, the first medical implant component may include an implant plate and the second medical implant component may include at least one implant fastener. In other embodiments, the first medical implant component and the second medical implant component may include other types of medical implants or medical implant components.

At block 106, a separation coating material is applied on at least one of the first implant contact surface on the first medical implant component and the second implant contact surface on the second medical implant component. In some embodiments, the separation coating material may be applied on the first implant contact surface and/or the second implant contact surface during manufacture of the first medical implant component and/or the second medical implant component. In some embodiments, the separation coating material may be applied on the first implant contact surface and/or the second implant contact surface during a surgical procedure. At block 108, the first medical implant component and the second medical implant component are fastened to bone with the separation coating material separating the first implant contact surface and the second implant contact surface. At block 110, the first medical implant component and the second medical implant component may be removed from the bone.

Figure 7:
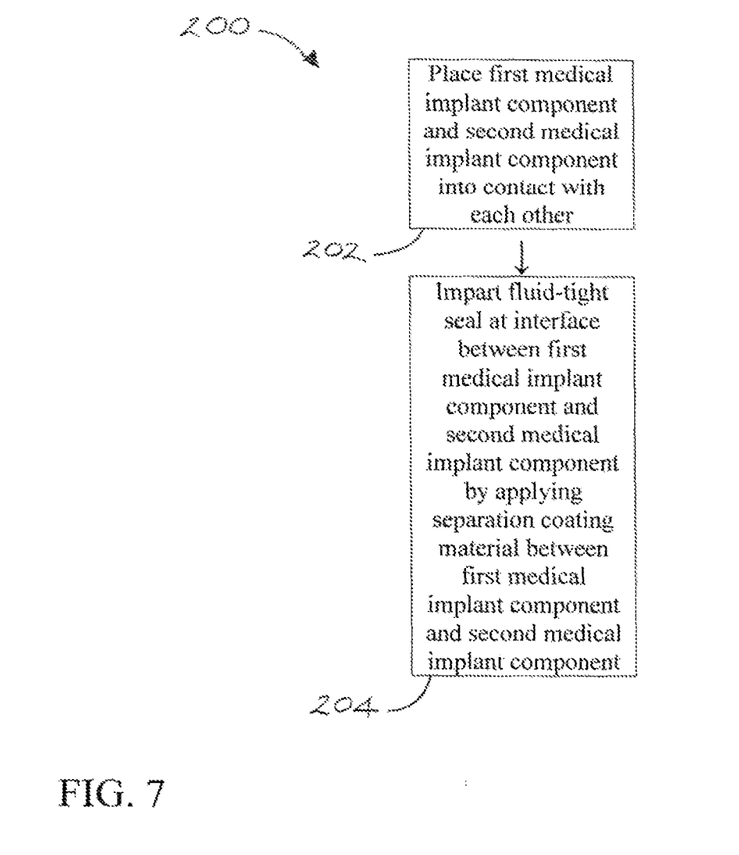
FIG. 7 is a flow diagram of an illustrative embodiment of a method of sealing an interface between a first implant component and a second implant component in a prosthesis system.

Referring next to FIG. 7 of the drawings, a flow diagram 200 of an illustrative embodiment of sealing an interface between a first implant component and a second implant component in a prosthesis system is illustrated. At block 202, a first medical implant component and a second medical implant component are placed into contact with each other. In some embodiments, the first medical implant component may include an acetabular shell and the second medical implant component may include at least one implant fastener. In some embodiments, the first medical implant component may include an implant plate and the second medical implant component may include at least one implant fastener. In other embodiments, the first medical implant component and the second medical implant component may include other types of medical implants or medical implant components. At block 204, a fluid-tight seal is imparted at an interface between the first medical implant component and the second medical implant component by applying a biocompatible separation coating material between the first implant component and the second implant component. The fluid-tight seal prevents fluids from entering the interface and corroding the first and second implant components.

While certain illustrative embodiments of the disclosure have been described above, it will be recognized and understood that various modifications can be made to the embodiments and the appended claims are intended to cover all such modifications which may fall within the spirit and scope of the disclosure.

What is claimed is:

1. A method for prevention of cold welding, corrosion, and tissue overgrowth between adjoined implant components subjected to static loading in a tin comprising:

obtaining a first medical implant component having a first implant contact surface;

obtaining a second medical implant component having a second implant contact surface, the second implant contact surface adapted for placement into contact with the first implant contact surface, the first implant contact surface and the second implant contact surface encompassing all points of contact between the first medical implant component and the second medical implant component; and applying a nonmetallic biocompatible separation coating material having a wax formulation on at least one of the first implant contact surface and the second implant contact surface using at least one of a smearing, spraying and immersion technique, the nonmetallic biocompatible separation coating material separates the first implant contact surface from the second implant contact surface at all of the points of contact between the first medical implant component and the second medical implant component;

wherein the wax formulation comprises ethylene combined with a copolymer wax, the copolymer wax including from about 5 percent to about 99 percent by weight of a co-monomer having molecular weight in the range of from about 500 to about 1,600 Dalton;

wherein the at least one of a smearing, spraying and immersion technique imparts a coating layer of the nonmetallic biocompatible separation coating material at an interface between the first and second medical implant components;

wherein the nonmetallic biocompatible separation coating material having a wax formulation is formulated to prevent cold welding, corrosion, and tissue overgrowth between the first medical implant component and the second medical implant component; and wherein obtaining a first medical implant component comprises obtaining an implant bone plate and obtaining a second medical implant component comprises obtaining at least one fastener configured to engage the implant bone plate.

2. The method of claim 1 wherein applying a nonmetallic biocompatible separation coating material having a wax formulation on at least one of the first implant contact surface and the second implant contact surface comprises applying a nonmetallic biocompatible separation coating material having a wax formulation on at least one of the first implant contact surface and the second implant contact surface during a surgical procedure.

3. The method of claim 2 wherein applying a nonmetallic biocompatible separation coating material having a wax formulation on at least one of the first implant contact surface and the second implant contact surface during a surgical procedure comprises applying a nonmetallic biocompatible separation coating material having a wax formulation on at least one of the first implant contact surface and the second implant contact surface using the smearing technique.

4. The method of claim 1 wherein applying a nonmetallic biocompatible separation coating material having a wax formulation on at least one of the first implant contact surface and the second implant contact surface comprises applying a nonmetallic biocompatible separation coating material having a wax formulation on at least one of the first implant contact surface and the second implant contact surface during manufacture of at least one of the first medical implant component and the second medical implant component, respectively.

* * * * *